United States Patent [19]
Ahrens et al.

[11] Patent Number: 5,651,067
[45] Date of Patent: Jul. 22, 1997

[54] STORAGE AND SELECTIVE INFORMATION TRANSMISSION SYSTEM FOR PERSONAL DATA

[75] Inventors: Wolfgang Ahrens, Kürten; Georg Hartmann, Köln; Gunnar Weikert, Düsseldorf, all of Germany

[73] Assignee: Bayer Aktiengesellschaft, Leverkusen, Germany

[21] Appl. No.: 385,862

[22] Filed: Feb. 9, 1995

[30] Foreign Application Priority Data

Feb. 16, 1994 [DE] Germany ............ 44 04 841.6

[51] Int. Cl.$^6$ .................................................. H04L 9/00
[52] U.S. Cl. .................................................. 380/25; 380/4
[58] Field of Search .................................. 380/4, 25, 47

[56] References Cited

U.S. PATENT DOCUMENTS

| | | |
|---|---|---|
| 4,905,277 | 2/1990 | Nakamura .................. 380/47 |
| 4,928,001 | 5/1990 | Massada . |
| 4,930,129 | 5/1990 | Takahira . |

FOREIGN PATENT DOCUMENTS

| | | |
|---|---|---|
| 3807997 | 9/1988 | Germany . |
| 3809028 | 9/1988 | Germany . |

OTHER PUBLICATIONS

"Metering Technologies for Digital Intellectual Property" Weber (Oct. 1994) pp. 1–29 INFRO.

*Primary Examiner*—Salvatore Cangialosi
*Attorney, Agent, or Firm*—Sprung Horn Kramer & Woods

[57] ABSTRACT

Storage and selective information transmission system of personal data comprising at least one optical memory card on which a defined memory field for storing a multiplicity of key terms is provided, a multiplicity of codes each assigned to at least one key term, at least one read/write device for the optical memory card having a multiplicity of key recognition functions, one key recognition function in each case pointing to one of a multiplicity of formatting functions contained in the read/write device and activating said formatting functions in interaction with the respective assigned code, each formatting function pointing to a data storage field of the optical card and being qualified, on the basis of the associated format specifications, for reading the data stored there.

3 Claims, 1 Drawing Sheet

STORAGE AND SELECTIVE INFORMATION TRANSMISSION SYSTEM FOR PERSONAL DATA

The present invention relates to a storage and selective information transmission system for personal data on the basis of an optical memory card.

Optical memory cards in a credit card format, which can be written ("WORM"=write once read many times memory) and read by means of laser beams, have reached storage capacities of several megabytes, especially from 4 to 6 megabytes, as a result of technical developments over the past years. A corresponding development has taken place in the read/write devices. In contrast to magnetic storage on diskettes the optically stored data are insensitive with respect to mechanical and electromagnetic effects. They are therefore suitable for being carried along, e.g. in purses, on the person. The read/write device necessary for writing and reading the card can be designed in the form of a handy accessory to personal computers which are already present in many households. The technology of the personal card which makes it possible to carry any information on one's person at all times is therefore available (e.g. U.S. Pat. No. 4,937,963).

Another advantage of the optical or magnetooptical card is that, if a card is lost or otherwise falls into the wrong hands, the stored data are not readily readable, the read/write device being required for this purpose.

Thus it has already been proposed (e.g. EP-A-467 693) to utilize the optical card for storing medical information, so that the doctor, in the event of a medical treatment, can inform himself on the anamnesis via the read/write device he has had installed. It had further been previously proposed to employ the optical card for storing X-ray pictures, so that the X-ray incidence and thus the dose commitment of the patient is reduced and moreover, if required, X-ray pictures remain continuously available over an extended period (DE-C 41 33 718, DE-A 42 03 447).

It would be desirable to carry on one's person, on the memory card, not only medical data but any conceivable personal data. For example, a problem which is frequently underestimated is that of personal files, insurance policies, certificates and the like being kept safely at home without protection against natural catastrophes (flood, fire, even theft), since such documents can often be replaced only with great difficulty and, depending on the type of the loss, the liquidation of insured damage is made more difficult if the insurer and the insurance number are not known.

The optical card is suitable for storing any such data. Its general introduction and acceptance is largely frustrated, however, by the present lack of data security, in that there is always the risk of, with each read operation, e.g. In the doctor's surgery, personal information also being made available which should be kept secret in the interest of the cardholder. Even if only medical data were to be stored, it is sometimes not in the interest of the patient, for example, to allow the dentist access to the internist's data. The possibility, in principle, of carrying on one's person a multiplicity of optical cards for various kinds of information storage would, on the one hand, militate against utilization of the high storage capacity of the card and, on the other hand, militate against the possibility of regularly carrying all the information on one's person.

There is therefore a need to provide a selective information transmission system on the basis of only one personal optical memory card, which enables authorization of access to specific data only, in each case, which are stored on the card and to exclude the other data from a read operation. The present invention therefore relates to a storage and selective information transmission system for personal data, comprising an optical memory card on which a spatially defined memory field for exclusive storage of a multiplicity of key terms is provided, furthermore in each case at least one further code is provided which in each case authorizes access to at least one key term each, at least one read/write device for the memory card having a multiplicity of key recognition functions, one key recognition function in each case pointing to one of a multiplicity of formatting functions (in the meaning of cryptography: decoding functions, which from the code in each time calculate decoding parameters, the decoding parameters enabling to decode data in the related data storage field, e.g. make them readable) and activating said formatting functions in interaction with the respective code, each formatting function pointing to a data storage field of the optical card and qualifying the read/write device for reading the data stored there. The code which now, in conjunction with the key term stored on the card, qualifies the read operation can be designed in such a way, e.g., that, in a manner specific to a key term, a code word or a code number (decoding parameter) are reported to the read/write device via a keyboard.

In a further preferred embodiment of the present invention, a code card, separate from the optical memory card, is provided which stores a multiplicity of code terms which are each assigned to at least one key term, and may be reported to the read/write device, e.g. via a code card reader having a read slot. The various code terms can thus be stored on the code card in the form of magnetic strips or optically readable bar codes. For example, the code card may contain bar codes, each parallel to the edges, on both sides, one bar code in each case, in interaction with at least one key term each, activating the read device.

The holder of the optical memory card can then let it out of his hands, for the purpose of making certain information available, and at the same time, by not letting the code card out of his hands but instead himself swiping it through the read slot by the desired side and edge, is himself able to make accessible only that optical memory field whose information content he wishes to transmit.

A further preferred embodiment of the present invention provides for the multiplicity of the codes which, in interaction with the key term of the optical memory card, activate the read device, each being designed in two parts, the two-part codes consisting of a standard password and a code term which is stored on the code card and is different in each case.

This ensures that, even if the memory card and the code card are lost at the same time, the lack of knowledge of the password makes access to the stored information impossible.

The interaction of key term and code in this context can be designed in such a way that, via an auxiliary program in the read/write device, the stored key term is converted in such a way, being processed by means of the code, that it points to a formatting function only after having been converted by means of the code.

In a further preferred embodiment of the present invention, the formatting function (decoding function) present in the read/write device is incomplete and is converted into the format specifications (decoding parameters) associated with the respective data storage field of the optical card only after the code has been read by an auxiliary program present in the read/write device.

This ensures that it is not possible, even by tampering with the read/write device set up on the part of the manufacturer for the interaction of key recognition functions and codes, for the read/write device to be set up for unauthorized reading of data storage fields.

On the part of the manufacturer, provision may be made to make certain key recognition and formatting functions available only to the read/write devices of certain persons. Thus, a data field for medical data of a specific indication may be provided, and a different data field for storing information on dates and place of safekeeping of a will. The associated key recognition functions and formatting functions can then be made available only to the doctors competent for said indication or to the notaries public competent with respect to wills, for the benefit of these persons' read/write devices. The read/write device can be secured in a customary manner against use by third parties via a password and/or a personal authorization card.

In addition, key terms and data fields can be provided on the optical memory card, which can be read by read devices, specially authorized for this person, even without the code, i.e. without the cooperation of the cardholder. Such data may, for example, be medical data which in the case of an accident have to be taken into account during initial treatment. Appropriate key recognition functions and formatting functions or format specifications would then be provided for the (and only the) read/write devices of the casualty departments and doctors on emergency call.

Figure 1:
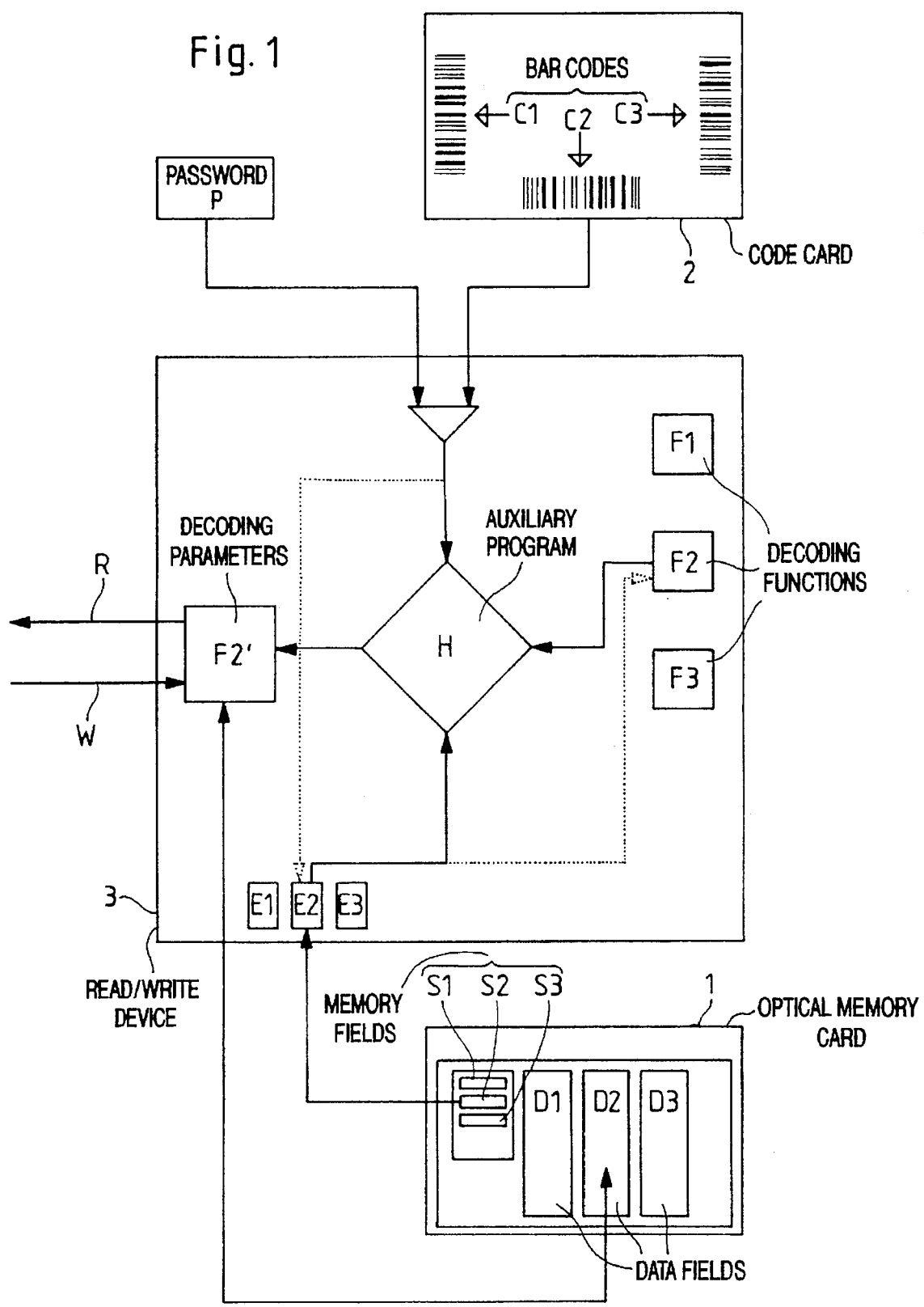
FIG. 1 is a diagram of the preferred embodiment

The invention is explained in more detail in its especially preferred embodiment with reference to FIG. 1. The optical memory card 1 contains a memory field for key terms S1, S2 and S3, and also data fields D1, D2 and D3 assigned to the respective key terms. The code card 2 at its edge contains bar codes C1, C2 and C3. The read/write device 3 contains formatting functions (decoding functions) F1, F2 and F3. Password P and code C2 are read into the read/write device 3 which further, via the key recognition function E2 reads the key S2. By processing P, C2 and S2 by means of the auxiliary program H, the formatting function (decoding function) F2 is converted into the format specifications (decoding parameters) F2', with the aid of which the memory field D2 of the optical memory card 1 (arrow R) can be read. Of course the field D2 is likewise written with the format specifications (coding parameters) F2' (arrow W) so that it is readable once more, as specified.

We claim:

1. Storage and selective information transmission system of personal data comprising at least one optical memory card (1) on which a defined memory field for storing a multiplicity of key terms (S1, S2, . . . ) is provided, a multiplicity of codes (C1, C2, . . . ) each assigned to at least one key term (S1, S2, . . . ), at least one read/write device (3) for the optical memory card (1) having a multiplicity of key recognition functions (E1, E2, . . . ), one key recognition function in each case addressing one of a multiplicity of formatting functions (F1, F2, . . . ) contained in the read/write device (3) and activating said formatting functions in interaction with the respective assigned code (C1, C2, . . . ), each formatting function addressing a data storage field (D1, D2, . . . ) of the optical card (1) and processed with the respective code (C1, C2, . . . ) and key term (S1, S2, . . . ) provides format specifications (F'1, F'2, . . . ) qualifying the read/write device (3) for reading the data stored in the respective data storage field (D1, D2, . . . ).

2. Information transmission system according to claim 1, in which the multiplicity of the codes (C1, C2, . . . ) are stored on a code card (2) assigned to the optical memory card (1).

3. Information transmission system according to claim 2, in which the codes (C1, C2, . . . ) cooperate with a common password (P).

* * * * *